(12) United States Patent
Taniguchi et al.

(10) Patent No.: US 12,180,442 B2
(45) Date of Patent: Dec. 31, 2024

(54) METHOD FOR AGGREGATING CELL MASS AND DEVICE FOR AGGREGATING CELL MASS

(71) Applicants: PUBLIC UNIVERSITY CORPORATION YOKOHAMA CITY UNIVERSITY, Kanagawa (JP); Japan Aerospace Exploration Agency, Tokyo (JP)

(72) Inventors: Hideki Taniguchi, Yokohama (JP); Tomomi Tadokoro, Yokohama (JP); Tetsuya Sakashita, Tokyo (JP); Satoshi Matsumoto, Tokyo (JP); Satoshi Adachi, Tokyo (JP); Akira Higashibata, Tokyo (JP)

(73) Assignees: PUBLIC UNIVERSITY CORPORATION YOKOHAMA CITY UNIVERSITY (JP); Japan Aerospace Exploration Agency (JP)

( * ) Notice: Subject to any disclaimer, the term of this patent is extended or adjusted under 35 U.S.C. 154(b) by 794 days.

(21) Appl. No.: 16/765,495

(22) PCT Filed: Nov. 30, 2018

(86) PCT No.: PCT/JP2018/044196
§ 371 (c)(1),
(2) Date: May 20, 2020

(87) PCT Pub. No.: WO2019/107546
PCT Pub. Date: Jun. 6, 2019

(65) Prior Publication Data
US 2020/0318044 A1    Oct. 8, 2020

(30) Foreign Application Priority Data
Nov. 30, 2017   (JP) ................. 2017-230609

(51) Int. Cl.
*C12N 5/00*   (2006.01)
*C12M 1/00*   (2006.01)
(Continued)

(52) U.S. Cl.
CPC ............ *C12M 21/08* (2013.01); *C12M 37/00* (2013.01); *C12M 41/48* (2013.01); *C12M 47/02* (2013.01);
(Continued)

(58) Field of Classification Search
None
See application file for complete search history.

(56) References Cited

U.S. PATENT DOCUMENTS

| 4,208,483 A | 6/1980 | Lee ............................. 435/284 |
| 5,989,913 A * | 11/1999 | Anderson .............. C12M 27/10 435/293.1 |
| 2003/0041800 A1 | 3/2003 | Uemura et al. ................ 117/200 |
| 2007/0116676 A1 | 5/2007 | Kida et al. ................... 424/93.7 |

(Continued)

FOREIGN PATENT DOCUMENTS

| JP | 2002-045173 A | 2/2002 |
| JP | 2003-070458 A | 3/2003 |

(Continued)

OTHER PUBLICATIONS

Grimm et al Tissue Engineering: Part B, vol. 20, No. 6, 2014, pp. 555-566 (Year: 2014).*

(Continued)

*Primary Examiner* — Evelyn Y Pyla
(74) *Attorney, Agent, or Firm* — OSTROLENK FABER LLP

(57) ABSTRACT

A method for aggregating cell masses includes performing a cell mass aggregating step of rotating a rotating body containing a specific gravity adjustment solution and cell masses to aggregate the cell masses, the specific gravity adjustment solution having biocompatibility, the cell masses (Continued)

having a lower specific gravity than the specific gravity adjustment solution.

7 Claims, 7 Drawing Sheets

(51) Int. Cl.
 *C12M 1/12* (2006.01)
 *C12M 1/36* (2006.01)
 *C12M 3/00* (2006.01)
 *C12N 5/071* (2010.01)
(52) U.S. Cl.
 CPC ......... *C12N 5/0062* (2013.01); *C12N 5/0697* (2013.01); *C12N 2535/10* (2013.01)

(56) References Cited

U.S. PATENT DOCUMENTS

| 2007/0131612 A1* | 6/2007 | Duffy, Jr. | G01N 15/042 210/600 |
| 2009/0258037 A1* | 10/2009 | Hammond | A61K 39/0275 506/10 |

FOREIGN PATENT DOCUMENTS

| JP | 2006-304791 A | 11/2006 |
| JP | 2008-237203 A | 10/2008 |
| JP | 2009-077708 A | 4/2009 |
| WO | WO 2005/056072 A1 | 6/2005 |
| WO | WO 2010/143651 A1 | 12/2010 |
| WO | WO 2013/077423 A1 | 5/2013 |
| WO | WO 2014/148592 A1 | 9/2014 |

OTHER PUBLICATIONS

Schulte et al., Processes 2014, 2(3), 526-547, published Jul. 8, 2014 (Year: 2014).*
Japanese Office Action, dated May 11, 2021, issued in corresponding Japanese Patent Application No. 2019-557352. English translation. Total 8 pages.
International Search Report mailed Feb. 12, 2019 in corresponding PCT International Application No. PCT/JP2018/044196.
Written Opinion mailed Feb. 12, 2019 in corresponding PCT International Application No. PCT/JP2018/044196.

* cited by examiner

METHOD FOR AGGREGATING CELL MASS AND DEVICE FOR AGGREGATING CELL MASS

CROSS-REFERENCE TO RELATED APPLICATIONS

The present application is a 35 U.S.C. §§ 371 national phase conversion of PCT/JP2018/044196, filed Nov. 30, 2018, which claims priority to Japanese Patent Application No. 2017-230609, filed Nov. 30, 2017, the contents of which are incorporated herein by reference. The PCT International Application was published in the Japanese language.

TECHNICAL FIELD

The present invention relates to a method for aggregating cell masses and a device for aggregating cell masses.

BACKGROUND ART

Conventionally, various treatments for a cell mass (spheroids, organoids) in a liquid culture medium (specific gravity adjustment solution) have been studied.

For example, the device for culturing cells described in Patent Document 1 (hereinafter also referred to as a culturing device) is a single-shaft rotary bioreactor having a gas exchange function. In the culturing device, a liquid culture medium is filled in a horizontal cylindrical bioreactor. After seeding cells (cell masses) in the liquid culture medium, culturing is performed while rotating the bioreactor along the horizontal axis of the bioreactor. Due to the rotation of the bioreactor, the direction of gravity applied to the cells (mass) in the bioreactor periodically changes, so that the cells are held in a relatively minute range with respect to the bioreactor. That is, sedimentation of the cells is suppressed. The cells are uniformly suspended in a liquid culture medium, cultured and grown for a required time, and fused to form a tissue mass.

Further, the culturing device described in Patent Document 2 uses a clinostat equipped with a liquid culture medium circulation system. The clinostat includes support columns installed on the main body, an outer frame, and an inner frame. The outer frame is rotatably supported with respect to the support columns. The inner frame is rotatably supported with respect to the outer frame. The culturing vessel rotates in the same manner as the inner frame. A liquid culture medium and cell masses to be cultured are sealed inside the culturing vessel. When each frame is rotated about the axes on which they are supported, the direction of gravity acting on the culturing vessel is dispersed, and the cell masses can proliferate and extend in all directions. Accordingly, three-dimensional culturing of the cell mass becomes possible.

PRIOR ART DOCUMENTS

Patent Documents

[Patent Document 1] PCT International Publication No. WO 2005/056072
[Patent Document 2] Japanese Unexamined Patent Application, First Publication No. 2006-304791

SUMMARY OF THE INVENTION

Problem to be Solved by the Invention

The culturing devices described in Patent Document 1 and Patent Document 2 each realize a microgravity environment in a culturing vessel and culture cell masses in the environment. However, in these culturing devices, there is a problem that the cell masses dispersed in the specific gravity adjustment solution cannot be aggregated at a predetermined position.

The present invention has been made in view of such a problem, and an object thereof is to provide a method for aggregating cell masses capable of aggregating cell masses at a predetermined position in a specific gravity adjustment solution, and a device therefor.

Means for Solving the Problem

In order to solve the above problem, the present invention proposes the following means.

A method for aggregating cell masses of the present invention includes: performing a cell mass aggregating step of rotating a rotating body containing a specific gravity adjustment solution and cell masses to aggregate the cell masses, the specific gravity adjustment solution having biocompatibility, the cell masses having a lower specific gravity than the specific gravity adjustment solution.

In addition, a device for aggregating cell masses according to the present invention includes: a rotating body configured to contain a specific gravity adjustment solution having biocompatibility and cell masses having a lower specific gravity than the specific gravity adjustment solution.

According to these inventions, when the rotating body is rotated, the cell masses move to a predetermined position in the specific gravity adjustment liquid with respect to the specific gravity adjustment liquid due to the centripetal force that arises from the difference between the specific gravity of the specific gravity adjustment liquid and the specific gravity of the cell masses. Since the specific gravity adjustment solution has biocompatibility, the cell masses collected at the predetermined position continue to survive in the specific gravity adjustment solution. Therefore, the cell masses can be aggregated at the predetermined position in the specific gravity adjustment solution.

In addition, in the method for aggregating cell masses, in the cell mass aggregating step, the rotating body may be rotated about a central axis of the rotating body to aggregate the cell masses around the central axis.

According to the present invention, the cell masses can be aggregated around the central axis.

In addition, in the above-described method for aggregating cell masses, the cell mass aggregating step may be performed in a state of a base material arranged on the central axis of the rotating body.

In addition, the above-described device for aggregating cell masses may include a mounting portion for mounting a base material on a central axis of the rotating body.

According to these inventions, cell masses can be aggregated around the base material.

In addition, in the above-described method for aggregating cell masses, the cell mass aggregating step may be performed while supplying a liquid culture medium into the base material.

In addition, the above-described device for aggregating cell masses may include a supply portion for supplying a liquid culture medium into the base material.

According to these inventions, nutrients, oxygen, and the like in the liquid culture medium can be supplied through the base material, and so necrosis of the cell mass can be suppressed.

In addition, the above-described method for aggregating cell masses may include performing a deaeration step of rotating the rotating body to collect air in the rotating body on the base material and remove the air from the rotating body through the base material.

According to the present invention, even if air is contained in the rotating body, it is possible to inhibit disturbances in the flow within the specific gravity adjustment liquid due to the air and it is possible to reliably aggregate cells.

In addition, in the method of aggregating cell masses, the deaeration step may be performed before the cell mass aggregating step.

According to the present invention, the cell masses can be more reliably aggregated from a state where there is no air in the rotating body.

In addition, in the above-described method for aggregating cell masses, the base material may be an artificial blood vessel or a regeneration blood vessel.

Effect of the Invention

According to the method for aggregating cell masses and the device for aggregating cell masses of the present invention, it is possible to aggregate cell masses at a predetermined position in a specific gravity adjustment solution.

EMBODIMENTS FOR CARRYING OUT THE INVENTION

Hereinbelow, an embodiment of a device for aggregating cell masses (hereinafter, also abbreviated as an aggregating device) according to the present invention will be described with reference to the drawings.

Figure 1:
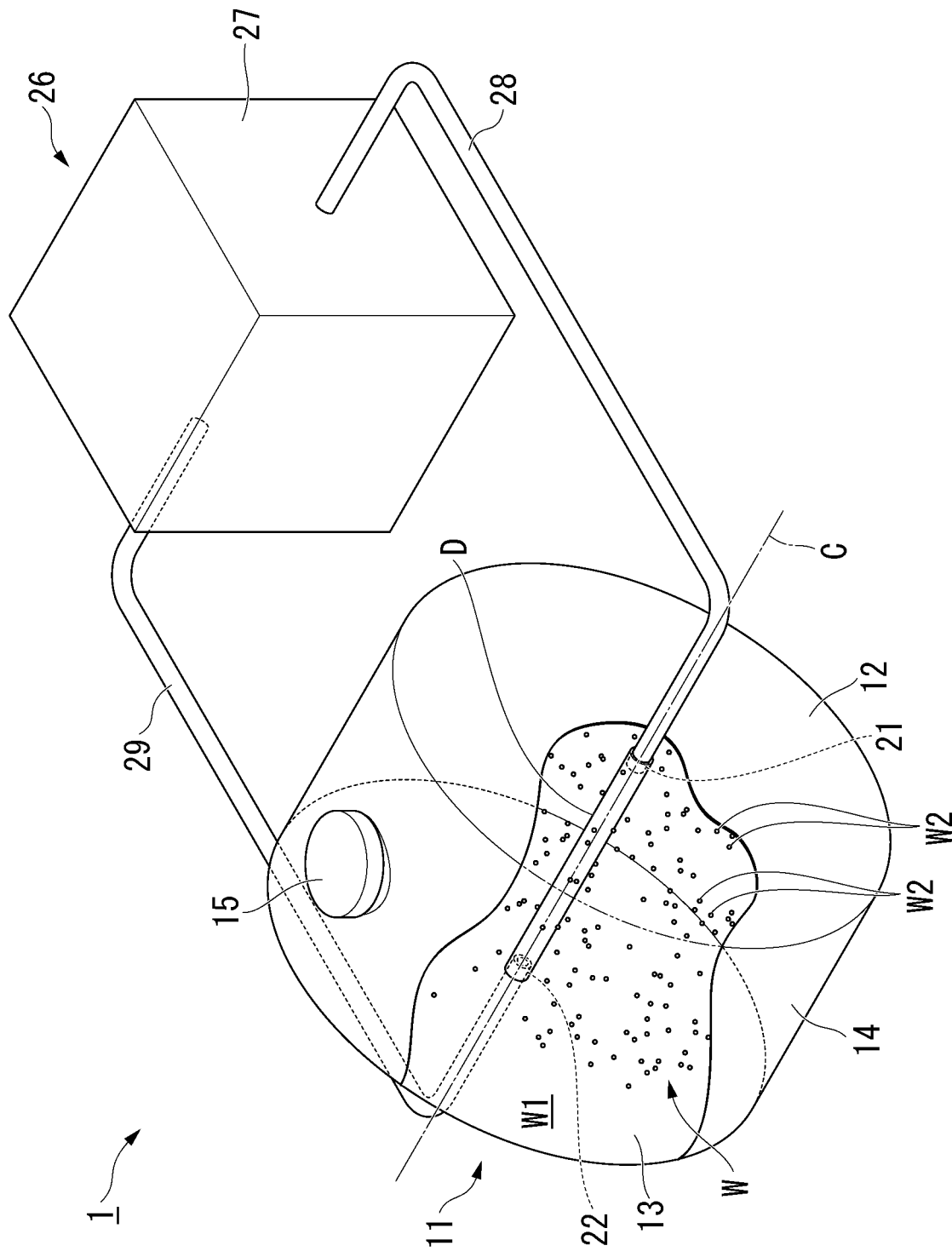
FIG. 1 is a partial cutaway perspective view of a device for aggregating cell masses according to an embodiment of the present invention.

As shown in FIG. 1, the aggregating device 1 of the present embodiment includes a rotating body 11, a pair of mounting portions 21 and 22, and a supply portion 26.

The shape of the rotating body 11 is not particularly limited as long as a housing space for housing a specific gravity adjustment solution and cells (cell masses) described later is formed. In the present embodiment, the rotating body 11 includes a first side portion 12, a second side portion 13, and an outer peripheral plate 14. The side portions 12 and 13 are formed in a circular shape and are arranged so as to face each other. The outer peripheral plate 14 is formed in a cylindrical shape. Each end of the outer peripheral plate 14 in the axial direction is connected to the outer peripheral edge of the first side portion 12 and the outer peripheral edge of the second side portion 13, respectively. The rotating body 11 is formed in a hollow cylindrical shape by resin or the like.

For example, an injection port 15 is formed in the outer peripheral plate 14 with rubber or the like. The injection port 15 penetrates the outer peripheral plate 14 and reaches the internal space of the rotating body 11. It is preferable that the rotating body 11 be provided with a lid that can be opened and closed. When the lid is closed, the lid is liquid-tightly connected to portions of the rotating body 11 other than the lid.

The material forming the side portions 12 and 13 and the outer peripheral plate 14 of the rotating body 11 is not particularly limited, and may be metal, acrylic resin, or the like. However, from the viewpoint of biocompatibility and internal visibility, it is preferable that the rotating body 11 be formed of resin by injection molding.

Cells referred to in the present specification are not particularly limited provided the cells can form spheroids, and for example include animal-derived cells, including mammals such as humans, monkeys, cows, horses, pigs, sheep, dogs, cats, rabbits, rats, mice, and hamsters. The cells may be established as cultured cells or primary cells obtained from biological tissues. As cells, it is possible to use neural stem cells or the like, as embryonic stem cells (ES cells), induced pluripotent stem cells (hereinafter referred to as iPS cells), and mesenchymal stem cells, and it is possible to use hepatocytes, pancreatic islet cells, kidney cells, nerve cells, corneal endothelial cells, chondrocytes, cardiomyocytes, and the like, as differentiated cells. Furthermore, cells that are induced to differentiate from cord blood, bone marrow, fat, and blood-derived tissue stem cells can also be used. Alternatively, cells that have become tumors, cells that have been transformed by genetic engineering techniques, or cells that have been infected with a viral vector can also be used.

The rotating body 11 is rotatably supported about a central axis C by a support table (not shown).

The rotating body 11 is rotated about the central axis C by a driving unit such as a motor. The driving unit transmits driving force by contacting the outer surface of the outer peripheral plate 14 of the rotating body 11 to rotate the outer surface thereof or by rotating a belt wound around a pulley fixed coaxially with the rotating body 11.

The mounting portions 21 and 22 are formed in a cylindrical shape, and are respectively arranged on the central axis C of the rotating body 11. The first mounting portion 21 is fixed to a surface of the first side portion 12 facing the second side portion 13. The second mounting portion 22 is fixed to a surface of the second side portion 13 facing the first side portion 12. A gap is formed between the first mounting portion 21 and the second mounting portion 22.

The mounting portions 21 and 22 are formed of the same material as the rotating body 11.

An artificial blood vessel (base material) D is attached to the mounting portions 21 and 22. The term "artificial blood vessel" as used herein means a blood vessel formed from synthetic fibers, biomaterials, or the like. The artificial blood vessel D is formed in a tubular shape from a material having gas permeability. The artificial blood vessel D is attached to the mounting portions 21 and 22 such as by fitting each end of the artificial blood vessel D to the mounting portions 21 and 22 from the outer side in the radial direction.

Although the base material is the artificial blood vessel D, the base material is not limited thereto, and may be a regenerated blood vessel or the like. The regeneration blood vessel mentioned here means a blood vessel formed by regenerative medicine.

A stock solution W is accommodated in the rotating body 11. The stock solution W includes a specific gravity adjustment solution W1 and cell masses W2.

Figure 2:
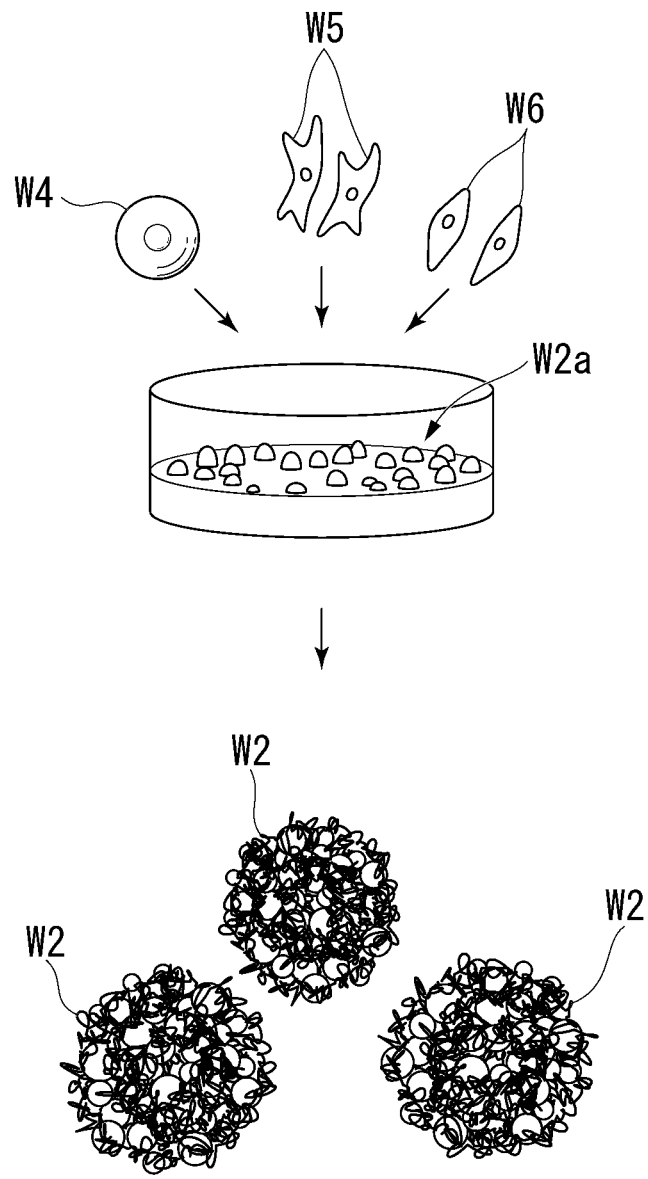
FIG. 2 is a perspective view for describing a step of generating cell masses by mixing cells derived from induced pluripotent stem cells, vascular endothelial cells, and mesenchymal cells.

As shown in FIG. 2, the cell mass W2 is obtained by aggregating and co-culturing in a well or a like a mixture W2a, which is obtained by mixing iPS cell-derived cells W4, vascular endothelial cells (HUVEC) W5, and mesenchymal cells (MSC) W6 at a predetermined ratio.

The term "vascular endothelial cell" as used herein means a cell constituting the vascular endothelium or a cell capable of differentiating into such a cell. The term "mesenchymal cell" as used herein means a connective tissue cell that mainly exists in the connective tissue derived from the mesoderm and forms a support structure for cells that function in a tissue, and is a concept that includes cells whose differentiation fate into mesenchymal cells has been determined but have not yet differentiated into mesenchymal cells.

The specific gravity of the cell mass W2 is smaller than the specific gravity of the specific gravity adjustment solution W1. For example, the specific gravity of the cell mass W2 is 1.05.

The specific gravity adjustment liquid W1 includes a first liquid culture medium and a biocompatible specific gravity adjustment agent. The specific gravity adjustment liquid W1 may include a pH adjustment agent, a suspending agent, and the like in addition to the first liquid culture medium and the specific gravity adjustment agent. The specific gravity adjustment agent W1 may be Iodixanol, FICOLL®, or the like.

The first liquid culture medium mentioned here and a second liquid culture medium described below are not particularly limited, and can be appropriately selected according to the cell (mass) to be cultured. Examples of publicly known culture media include MEM, α-MEM, DMEM, RPM1, cRDF, ERDF, F12, MCDB131, F12/DMEM, and WE. When the cells are human stem cells, MTESR1 (manufactured by Stem Cell Tech.), ESSENTIAL 8® (manufactured by Life Technologies), REPRO FF/FF2/XF (manufactured by Reprocell), STEMSURE® (manufactured by Wako Pure Chemical Industries, Ltd.), CELRENA (manufactured by Cell Science & Technology Institute), S-MEDIUM (manufactured by DS Pharma), STEMFIT (manufactured by Ajinomoto) and the like, which are commercially available as medium for human totipotent stem cells, can be used.

In addition, the term "biocompatibility" as used herein means not imparting a strong adverse effect or strong stimulus to a living body, and therefore means the attribute of being capable of coexisting with at least one of a biological component, a biological tissue such as a cell (lump), and a substance derived from an organism.

For example, as the first liquid culture medium, one that differentiates the cell mass W2 into a liver cell is used. The specific gravity of the first liquid culture medium is about 1.0.

The specific gravity adjustment agent is preferably a density gradient medium for cell separation. OPTIPREP® (manufactured by Cosmo Bio Inc.) is used as a density gradient medium. For example, the specific gravity of the specific gravity adjustment liquid W1 is 1.06 or more and 1.08 or less. However, if the specific gravity of the cell mass W2 is smaller than the specific gravity of the specific gravity adjustment solution W1, the specific gravity of the specific gravity adjustment solution W1 can be, for example, 1.03 or more and 1.15 or less, or 1.01 or more and 1.20 or less.

The concentration of the specific gravity adjustment agent in the specific gravity adjustment solution W1 is preferably such that the specific gravity adjustment solution W1 does not harm the cell mass W2.

As shown in FIG. 1, for example, the supply portion 26 includes a main body 27, a supply pipe 28, and a discharge pipe 29. The supply pipe 28 and the first mounting portion 21 communicate with each other. The discharge pipe 29 and the second mounting portion 22 communicate with each other.

For example, although not shown, the main body 27 includes a supply tank, a pump, and a waste tank. A second liquid culture medium (liquid culture medium) is contained in the supply tank. The second liquid culture medium is not particularly limited, but may be the same as the first liquid culture medium.

The pump supplies the second liquid culture medium in the supply tank to the supply pipe 28 at a constant flow rate. The supply portion 26 supplies the second liquid culture medium into the rotating body 11. The used second liquid culture medium returned to the main body 27 through the discharge pipe 29 is stored in the waste tank.

The supply unit 26 may supply blood, artificial blood, or the like instead of the second liquid culture medium.

Figure 3:
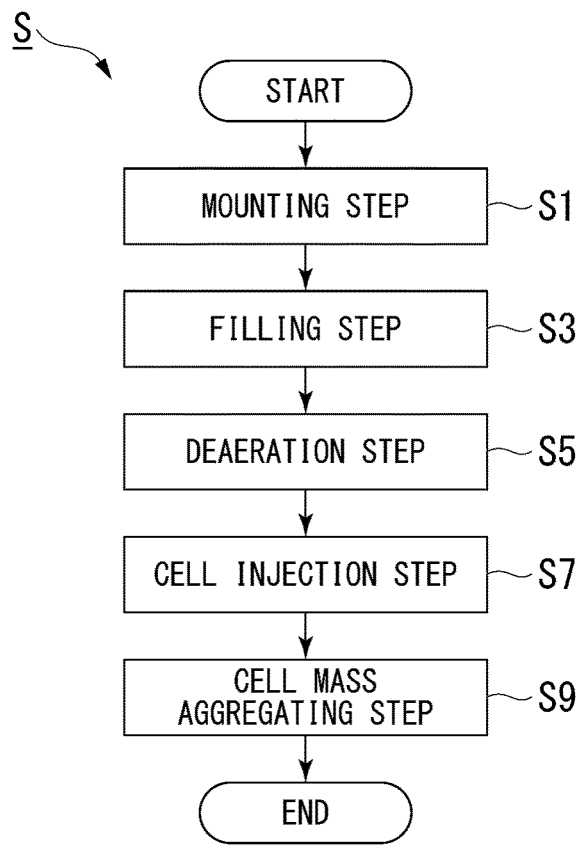
FIG. 3 is a flowchart showing a method for aggregating cell masses according to an embodiment of the present invention.

Next, a method for aggregating cell masses (hereinafter, also abbreviated as an aggregating method) according to the present embodiment will be described. FIG. 3 is a flowchart showing the aggregating method S according to the embodiment of the present invention.

First, in the mounting step (Step S1 shown in FIG. 3), the lid of the rotating body 11 is opened, and each end of the artificial blood vessel D is fitted onto the mounting portions 21 and 22. Thereby, the artificial blood vessel D is arranged on the central axis C of the rotating body 11. The space between each end of the artificial blood vessel D and the attachment portions 21 and 22 is sealed in a liquid-tight manner. After the placement of the artificial blood vessel D, the lid of the rotating body 11 is closed. When the mounting step S1 is completed, the process proceeds to Step S3.

Next, in the filling step (Step S3), the rotating body 11 is filled with the specific gravity adjustment liquid W1 through the injection port 15 using a syringe or the like. At this time, it is preferable to fill the specific gravity adjustment liquid W1 so that no air bubbles remain in the rotating body 11.

Next, in the deaeration step (Step S5), the rotating body 11 containing the specific gravity adjustment liquid W1 is rotated about the central axis C by the driving unit. Since the specific gravity of the air is smaller than the specific gravity of the specific gravity adjustment liquid W1, the air moves from the outer side in the radial direction of the central axis C toward the central axis C with respect to the specific gravity adjustment liquid W1 due to the centripetal force acting on the air. The air in the rotating body 11 is collected on the artificial blood vessel D. Since the artificial blood vessel D has gas permeability, air is removed from the inside of the rotating body 11 through the blood vessel wall of the artificial blood vessel D into the artificial blood vessel D.

This deaeration step S5 is performed before a cell mass aggregating step S9 described below.

Next, in the cell injection step (Step S7), a plurality of the cell masses W2 are injected into the rotating body 11 through the injection port 15 using a syringe or the like. Since the specific gravity adjustment liquid W1 in the rotating body 11 has biocompatibility, the plurality of cell masses W2 can continue to survive in the specific gravity adjustment liquid W1.

Figure 4:
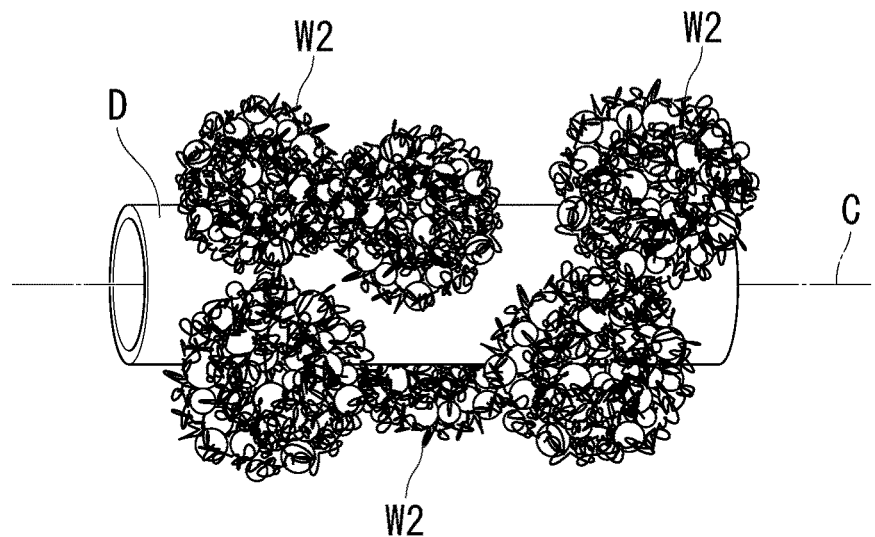
FIG. 4 is a perspective view for describing a state in which a plurality of cell masses are aggregated on an artificial blood vessel by cell masses aggregating step in the method for aggregating cell masses.

Next, in the cell mass aggregating step (Step S9), the rotating body 11 containing the specific gravity adjustment liquid W1 and the plurality of cell masses W2 is rotated about the central axis C by the driving portion. Since the specific gravity of the cell mass W2 is smaller than the specific gravity of the specific gravity adjustment solution W1, the plurality of the cell masses W2 move toward the central axis C with respect to the specific gravity adjustment solution W1 due to the centripetal force acting on the cell masses W2. As shown in FIG. 4, the plurality of cell masses W2 aggregate on the outer peripheral surface of the artificial blood vessel D, which is arranged on the central axis C.

The cell mass aggregating step S9 may be performed while the supply portion 26 supplies the second liquid culture medium into the artificial blood vessel D. By doing so, nutrients, oxygen, and the like in the second liquid culture medium are supplied to the cell masses W2.

With the above, all steps of the aggregating method S are completed.

If the aggregating method S of the present embodiment is performed in a place where gravity does not act, such as in outer space, or a place where only gravity smaller than the gravity of the earth acts, even if the rotating body 11 does not rotate about the central axis C, the cell masses W2 hardly settle in the specific gravity adjustment solution W1. By rotating the rotating body 11 about the central axis C, the cell masses W2 can be aggregated in a stable manner.

(Simulation Result)

Hereinbelow, a description will be given of a result of simulating a state in which a plurality of the cell masses W2 move in the rotating body 11, which rotates on ground where gravity acts.

The diameter of the rotating body 11 was set to 20 mm and the thickness was set to 10 mm, while the thicknesses of the side portions 12 and 13 and the outer peripheral plate 14 were ignored. It was assumed that the rotating body 11 was arranged such that the central axis C was along the horizontal plane.

The diameter of the cell mass W2 was set to 100 μm (micrometers) and the specific gravity was set to 1.05. The number of cell clusters W2 supplied into the rotating body 11 was set to 600. The specific gravity of the specific gravity adjustment liquid W1 was set to 1.08. The diameter of the artificial blood vessel D was set to 1 mm. It was assumed that gravity acted at 1 G (9.8 m/s$^2$) toward the lower part A shown in FIG. 5. The rotation speed of the rotating body 11 about the central axis C was set to 150 rpm (rotations/minute).

Figure 5:
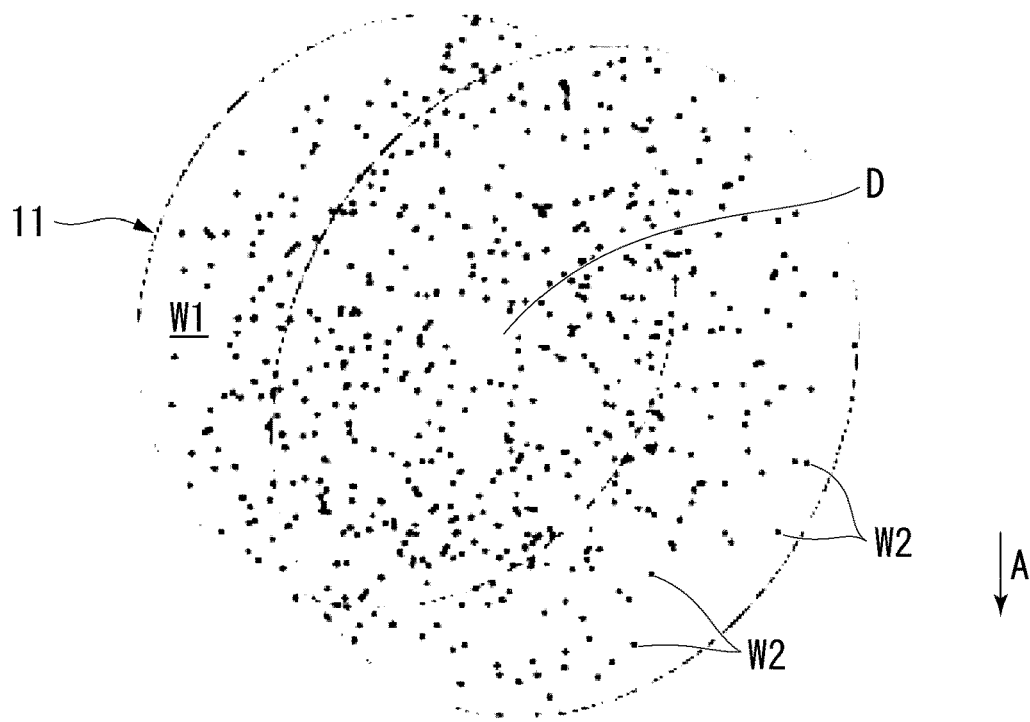
FIG. 5 is a perspective view showing a simulation result of the method for aggregating cell masses, showing a state before the rotating body rotates.
Figure 6:
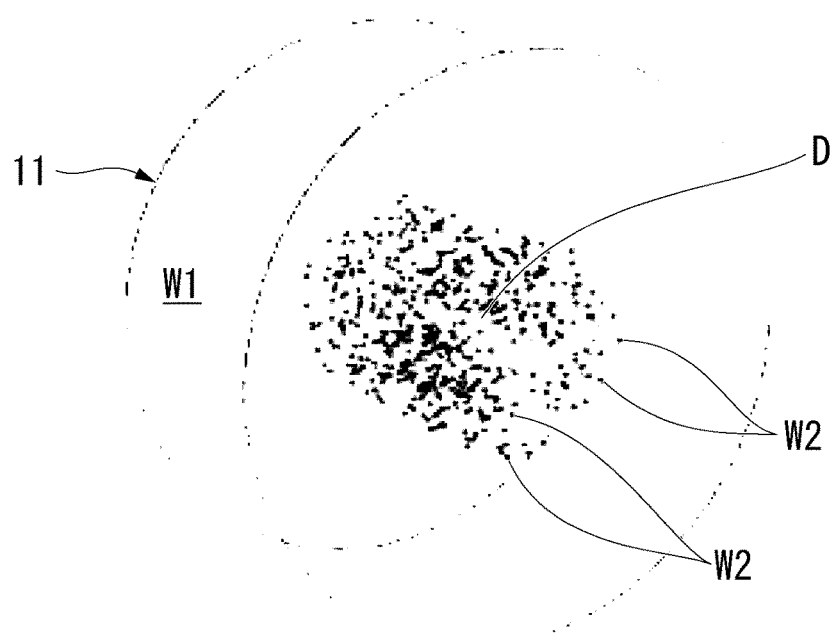
FIG. 6 is a perspective view showing a simulation result of the method for aggregating cell masses, showing a state four minutes after rotation of the rotating body.
Figure 7:
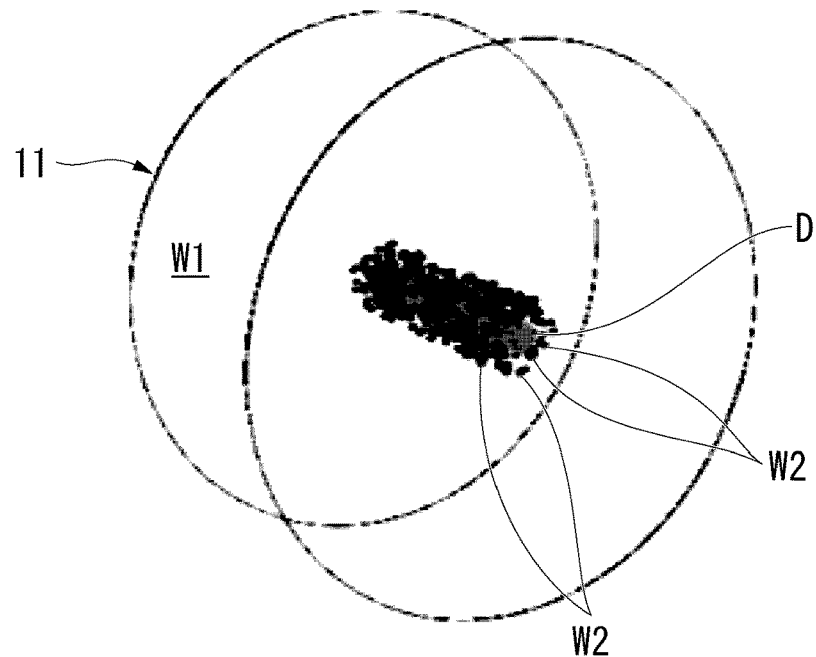
FIG. 7 is a perspective view showing a simulation result of the method for aggregating cell masses, showing a state eight minutes after rotation of the rotating body.
Figure 8:
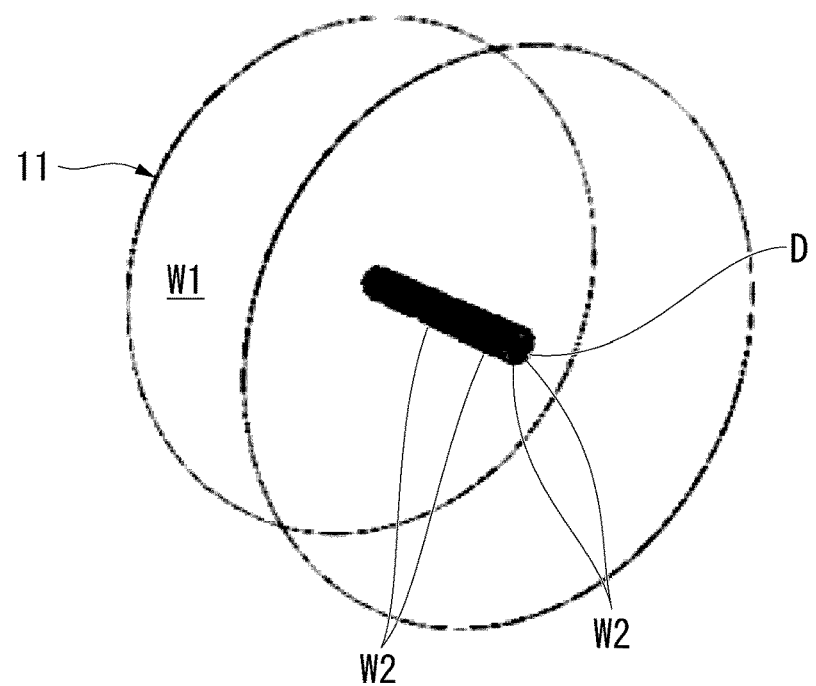
FIG. 8 is a perspective view showing a simulation result of the method for aggregating cell masses, showing a state 12 minutes after rotation of the rotating body.

In the initial state before the rotating body 11 rotates, as shown in FIG. 5, it is assumed that the plurality of cell masses W2 are substantially uniformly dispersed in the specific gravity adjustment solution W1. FIGS. 6, 7, and 8 show the state where the rotating body 11 has rotated about the central axis C for 4, 8, and 12 minutes, respectively. As the time of the rotating body 11 rotating about the central axis C increases, the plurality of cell masses W2 move so as to approach the artificial blood vessel D. It was found that, in the state shown in FIG. 8 rotated for 12 minutes, the cell masses W2 aggregated around the artificial blood vessel D.

As described above, according to the aggregation method S and the aggregation device 1 of the present embodiment, when the rotating body 11 is rotated about the central axis C, the plurality of cell masses W2 move toward the central axis C from the outer side in the radial direction of the central axis C with respect to the specific gravity adjustment liquid W1 due to the centripetal force that arises from a difference between the specific gravity of the specific gravity adjustment solution W1 and the specific gravity of the cell mass W2. Since the specific gravity adjustment solution W1 has biocompatibility, a plurality of the cell masses W2 can be aggregated on the central axis C while still living.

The cell mass aggregating step S9 is performed in a state in which the artificial blood vessel D is arranged on the central axis C of the rotating body 11 by the mounting portions 21 and 22. Thereby, a plurality of cell masses W2 can be aggregated on the artificial blood vessel D.

The cell mass aggregating step S9 is performed while supplying the second liquid culture medium into the artificial blood vessel D by the supply portion 26. Therefore, nutrients, oxygen, and the like in the second liquid culture medium can be supplied to the plurality of cell masses W2 through the artificial blood vessel D.

The deaeration step S5 is performed in the aggregating method S. Accordingly, even if air is contained in the rotating body 11, by inhibiting disturbances in the flow within the specific gravity adjustment liquid W1 due to the air, the cell masses W2 can be reliably aggregated.

The deaeration step S5 is performed before the cell mass aggregating step S9. Accordingly, the cell masses W2 can be more reliably aggregated in the cell mass aggregating step S9 from the state where there is no air in the rotating body 11.

One embodiment of the present invention has been described in detail above with reference to the drawings. However, a specific configuration is not limited to this embodiment, with other changes, combinations and omissions of the constitution within a range not departing from the gist of the present invention also being included.

For example, in the above-described embodiment, the aggregating device 1 may not include the mounting portions 21 and 22. In this case, the mounting step S1 is not performed in the aggregating method S. When the cell masses W2 are aggregated without mounting the artificial blood vessel D, the cell masses W2 aggregate around the central axis C (on the central axis C). When the centripetal force on the central axis C is weak, the cell masses W2 aggregate in a tubular shape.

The aggregating device 1 may not include the supply portion 26. In the aggregating method S, the deaeration step S5 may be performed simultaneously with the cell mass aggregating step S9, and the deaeration step S5 may not be performed.

When the specific gravity of the cell masses W2 is smaller than the specific gravity of the specific gravity adjustment liquid, the specific gravity adjustment liquid may include the first liquid culture medium without including the specific gravity adjustment agent.

WORKING EXAMPLES

Hereinbelow, working examples and comparative examples of the present invention will be shown in detail and be described, but the present invention is not limited to the following working examples.

As shown in Table 1, Sample Nos. 1 to 6 were examined as specific gravity adjustment agents.

Figure 9:
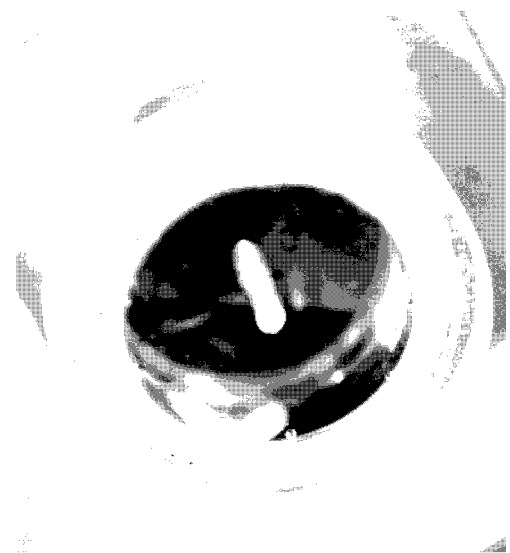
FIG. 9 is a photograph showing a perspective view of a state in which the rotating body having been rotated in the state of the rotating body filled with a specific gravity adjustment liquid and a plurality of cell masses injected therein.

An artificial blood vessel was placed on the central axis of the rotating body. Hepatic progenitor cells derived from iPS cells, vascular endothelial cells and mesenchymal cells were mixed at a predetermined ratio to prepare the cell masses. As shown in FIG. 9, the rotating body was filled with the specific gravity adjustment liquid, and the rotating body was rotated in a state in which a plurality of cell masses were injected. The rotating body was rotated at a rotation speed of 150 rpm for 12 minutes.

The criteria for determining a specific gravity adjustment agent (specific gravity adjustment liquid) as being acceptable are that the specific gravity adjustment agent has biocompatibility, has a higher specific gravity than the cell mass, and that a plurality of cell masses survive in the specific gravity adjustment agent.

TABLE 1

| Sample No. | Specific gravity adjustment agent | Concentration of specific gravity adjustment agent | Specific gravity of specific gravity adjustment solution | pH of specific gravity adjustment solution |
|---|---|---|---|---|
| 1 | Lymphocyte Separation Solution | 70% | 1.06 | 7.8 |
| 2 | OptiPrep | 14% | 1.06 to 1.07 | 7.8 |
| 3 | OptiPrep | 15% | 1.07 to 1.08 | 7.8 |
| 4 | Percoll | 70% | 1.07 to 1.08 | 8.1 |
| 5 | Sodium polytungstate | 6 to 8% | 1.06 | 6.6 |
| 6 | Methyl cellulose | 0.10% | 0.98 | — |

Working Example 1

As the specific gravity adjustment agent, Lymphocyte Separation Solution (manufactured by Nacalai Tesque Inc.) of Sample No. 1 was mixed with the first liquid culture medium at 70% (% by weight) to prepare a specific gravity adjustment solution. In this case, 30% of the specific gravity adjustment liquid is the first liquid culture medium. The specific gravity of the specific gravity adjustment solution was 1.06, and the pH was 7.8. As a result of filling the rotating body with the prepared specific gravity adjustment solution and rotating the rotating body, it was found that a plurality of the cell masses survived and so a passing evaluation was given.

Working Example 2

Figure 10:
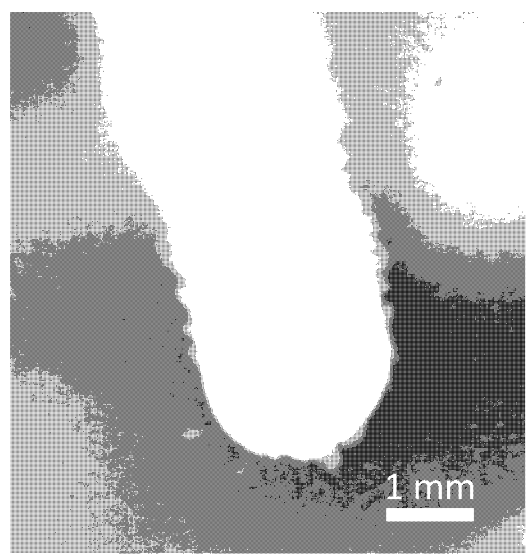
FIG. 10 is a photograph showing a perspective view of a state in which cell masses are aggregated on the artificial blood vessel.
Figure 11:
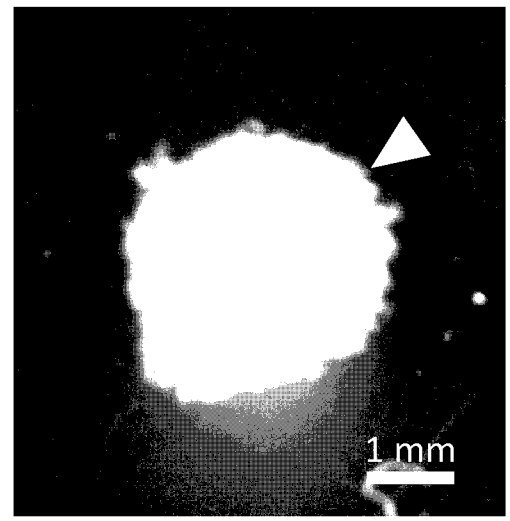
FIG. 11 is a photograph showing a state, viewed from the front, in which cell masses are aggregated on the artificial blood vessel.
Figure 12:
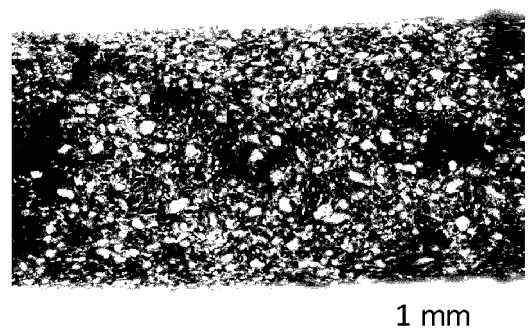
FIG. 12 is a photograph showing a state, viewed from the side, in which cell masses retain fluorescence expression.

As the specific gravity adjustment agent, OPTIPREP® (manufactured by Cosmo Bio Company, Limited) of Sample No. 2 was mixed with the first liquid culture medium at 14% to prepare a specific gravity adjustment liquid. The specific gravity of the specific gravity adjustment solution was 1.06 to 1.07, and the pH was 7.8. As a result of filling the rotating body with the prepared specific gravity adjustment solution and rotating the rotating body, cell masses including vascular endothelial cells expressing Kusabira-Orange, mesenchymal cells, and hepatic progenitor cells derived from TkDA 3-4 cells (iPS cells) that expressed EGFP aggregated on the artificial blood vessel, as shown in FIGS. 10 and 11. At this time, as shown in FIG. 12, it was found that a plurality of cell masses maintained fluorescence expression, that is, survived, and so a passing evaluation was given.

Working Example 3

As the specific gravity adjustment agent, OptiPrep of Sample No. 3 was mixed with the first liquid culture medium at 15% to prepare a specific gravity adjustment liquid. The specific gravity of the specific gravity adjustment solution was 1.07 to 1.08, and the pH was 7.8. As a result of filling the rotating body with the prepared specific gravity adjustment solution and rotating the rotating body, vascular endothelial cells, mesenchymal cells, and TkDA 3-4 cells expressing EGFP were found to slightly differ from the normal form, but a plurality of the cell masses survived, and so a passing evaluation was given.

Working Example 4

As the specific gravity adjustment agent, PERCOLL® (manufactured by GE Healthcare Co., Ltd.) of Sample No. 4 was mixed with the first liquid culture medium at 70% to prepare a specific gravity adjustment liquid. The specific gravity of the specific gravity adjustment solution was 1.07 to 1.08, and the pH was 8.1. As a result of filling the rotating body with the prepared specific gravity adjustment solution and rotating the rotating body, the vascular endothelial cells and mesenchymal cells were found to slightly differ from the normal form, but a plurality of cell masses survived, and so a passing evaluation was given.

Comparative Example 1

As the specific gravity adjustment agent, sodium polytungstate of Sample No. 5 was mixed with the first liquid culture medium at 6% to 8% to prepare a specific gravity adjustment liquid. The specific gravity of the specific gravity adjustment solution was 1.06, and the pH was 6.6. As a result of filling the rotating body with the prepared specific gravity adjustment solution and rotating the rotating body, the cell masses were found to have peeled off from the artificial blood vessel and the cell masses were necrotic. Multiple cell masses could not survive and so a failing evaluation was given.

Comparative Example 2

As the specific gravity adjustment agent, methyl cellulose of Sample No. 6 was mixed with the first liquid culture medium at 0.10% to prepare a specific gravity adjustment liquid. The specific gravity of the specific gravity adjustment liquid was 0.98. Since a specific gravity adjustment solution having a specific gravity lower than that of cell masses was not anticipated, a failing evaluation was given.

INDUSTRIAL APPLICABILITY

The method for aggregating cell masses and the device for aggregating cell masses according to the present embodiment can be suitably used for aggregating cell masses.

REFERENCE SYMBOLS

1: Aggregating device (device for aggregating cell masses)
11: Rotating body
21: First mounting portion (mounting portion)
22: Second mounting portion (mounting portion)
26: Supply portion
C: Central axis
D: Artificial blood vessel
S: Aggregating method (method for aggregating cell masses)
S5: Deaeration step
S9: Cell mass aggregating step
W1: Specific gravity adjustment liquid
W2: Cell mass

The invention claimed is:

1. A method for aggregating cell masses, comprising:
the step of attaching a first end and a second end of a tubular shaped base material that is an artificial blood vessel or a regeneration blood vessel, respectively, to a first mounting portion and a second mounting portion that are arranged on a central axis of the rotating body and are spaced apart from each other, to linearly extend the base material on the central axis from the first end to the second end without bending the base material and to connect the first mounting portion and the second mounting portion via the artificial base material; and
a cell mass aggregating step of rotating at the rotation speed a rotating body containing a specific gravity adjustment solution and cell masses and aggregating the cell masses on an outer surface of the base material by centripetal force acting on the cell masses due to rotation of the rotating body and difference in specific gravity between the specific gravity adjustment solution and the cell masses, the specific gravity adjustment solution having biocompatibility, the cell masses having a lower specific gravity than the specific gravity adjustment solution, and the rotation speed being selected to cause cell aggregation by the centripetal force.

2. The method for aggregating cell masses according to claim 1, wherein in the cell mass aggregating step, the rotating body is rotated about the central axis of the rotating body to aggregate the cell masses around the central axis.

3. The method for aggregating cell masses according to claim 1, wherein the cell mass aggregating step is performed while supplying a liquid culture medium into the base material.

4. The method for aggregating cell masses according to claim 1, further comprising a deaeration step of rotating the rotating body in which air is contained, collecting the air on the base material by centripetal force acting on the air due to rotation of the rotating body and difference in specific gravity between the specific gravity adjustment solution and the air, and removing the air from the rotating body by the air passing through the base material having gas permeability.

5. The method for aggregating cell masses according to claim 4, wherein the deaeration step is performed before the cell masses are injected into the rotating body.

6. The method for aggregating cell masses according to claim 1, wherein the specific gravity adjustment solution includes a liquid culture medium.

7. The method for aggregating cell masses according to claim 1, the method comprising completely covering the outer surface of the base material with uniformly arranged vascular organoids using the centripetal force, and culturing vascular organoids to form and mature a surface vascular network.

* * * * *